United States Patent [19]
Seyedin et al.

[11] 4,434,094
[45] Feb. 28, 1984

[54] PARTIALLY PURIFIED OSTEOGENIC FACTOR AND PROCESS FOR PREPARING SAME FROM DEMINERALIZED BONE

[75] Inventors: Saeid Seyedin, Mt. View; Thomas Thomas, Palo Alto, both of Calif.

[73] Assignee: Collagen Corporation, Palo Alto, Calif.

[21] Appl. No.: 484,286

[22] Filed: Apr. 12, 1983

[51] Int. Cl.$^3$ ............................................. C07G 7/00
[52] U.S. Cl. ........................... 260/112 R; 260/123.7; 260/118; 424/95; 424/177
[58] Field of Search .................. 260/112 R, 123.7, 118

[56] References Cited
U.S. PATENT DOCUMENTS 3,539,549 11/1970 Greenfield ..................... 260/112 R
4,294,753 10/1981 Urist .............................. 260/112 R

OTHER PUBLICATIONS

Urist et al., Clin. Orthopaedics and Related Research, (1982), 162, 219–232.

Primary Examiner—Howard E. Schain
Attorney, Agent, or Firm—Ciotti & Murashige

[57] ABSTRACT

A process for partially purifying an osteogenic factor from demineralized bone particles in which nonfibrous proteins are extracted from the demineralized bone with a dissociative extractant for nonfibrous proteins, such as urea or guanidine hydrochloride, the extracted nonfibrous proteins are fractionated by anion exchange chromatography using DEAE cellulose at pH 7, the fraction not adsorbed by the DEAE cellulose is further fractionated by cation exchange chromatography using CM cellulose at pH 4.8, the fraction adsorbed by the CM cellulose is eluted therefrom and the partially purified osteogenic factor is recovered from the eluate as a $\leq 30,000$ dalton protein isolate.

10 Claims, 2 Drawing Figures

PARTIALLY PURIFIED OSTEOGENIC FACTOR AND PROCESS FOR PREPARING SAME FROM DEMINERALIZED BONE

DESCRIPTION

1. Technical Field

The invention is in the fields of protein chemistry and osteoplasty. More particularly the invention relates to a partially purified extract from demineralized bone that exhibits cartilage and bone induction activity.

2. Background Art

Prior efforts to isolate and characterize the chemical or chemicals present in bone that induce osteogenesis have been reported. U.S. Pat. No. 4,294,753 describes the partial isolation of a bone inducing agent, called "bone morphogenetic protein," from demineralized bone. Bone morphogenetic protein was not fully characterized and was obtained as a crude bone or dentin tissue extract. The process by which the crude protein was obtained involved: demineralizing bone tissue; extracting the factor from the demineralized bone with an aqueous solution of a neutral salt and either urea or guanidine; and removing the urea or guanidine from the extract to precipitate the crude protein.

Ion exchange purification of crude bone morphogenetic protein is reported by Urist, M. R., et al., *Clin Orthopaedics and Related Research* (1982) 162:219–232. The crude protein was redissolved and reprecipitated in 6 M and 1 M aqueous urea, respectively. The final precipitates was taken up in 6 M urea and chromatographed on CM-cellulose (a cationic exchanger) at pH 4.8. The unadsorbed fraction was further chromatographed on DEAE-cellulose (an anion exchanger) at pH 7.2. Bioassays of the adsorbed and unadsorbed fractions from both separations showed that only the unadsorbed fractions from each separation exhibited osteoinductive activity. High molecular weight proteins were separated from the DEAE unadsorbed fraction by gel filtration.

A principal object of the present invention is to provide a partially purified osteogenic factor that is either different from or purer than the factor reported by Urist, et al.

DISCLOSURE OF THE INVENTION

The osteogenic factor of the invention is present in vertebrate bone and has the following characteristics:

(a) it is a nonfibrous protein;

(b) it is unadsorbed by diethylaminoethyl cellulose anion exchanger at a pH of about 7.0;

(c) it is adsorbed by carboxymethyl cellulose cation exchanger at a pH of about 4.8; and (d) it has a molecular weight below about 30,000 daltons.

The process for partially purifying this osteogenic factor from particulate demineralized bone comprises:

(a) extracting nonfibrous proteins from demineralized bone with a liquid dissociative nonfibrous protein extractant;

(b) contacting the extract of (a) with an anion exchanger at a pH of about 6.8 to about 7.2;

(c) contacting the unadsorbed fraction of the extract with a cation exchanger at a pH of about 4.5 to about 5.2;

(d) eluting the adsorbed fraction from the cation exchanger; and (e) isolating materials having a molecular weight below about 30,000 daltons from the eluate of (d).

MODES FOR CARRYING OUT THE INVENTION

Figure 1:
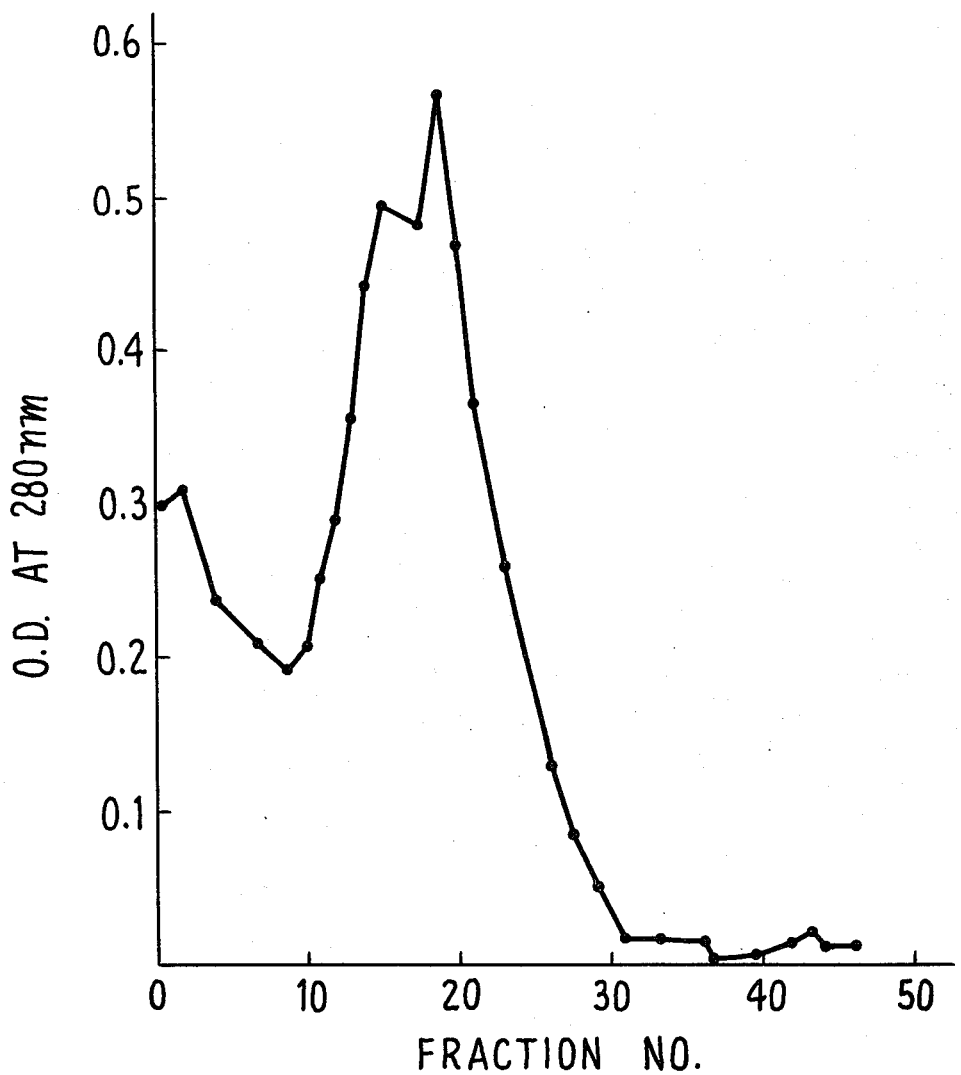
FIG. 1 is a graph of the optical densities of eluate fractions from the preparative ion exchange of the example, infra.

The bone that is used in the invention may be collected from a variety of mammalian sources. Homogeneic and xenogeneic sources may be used. Bovine and porcine bone, preferably long bone, will normally be used because of its availability. The surface of the bone is first cleaned by physically removing periosteum by scraping or brushing. The bone is then fragmented or pulverized into small pieces and the fragments are washed with a very mild aqueous acid, eg, 0.01 N HCl, with agitation to remove any water soluble materials remaining on the fragments. The washing is preferably carried out at a reduced temperatures, usually about 0° C. to 18° C., preferably about 5° C., with frequent changing of the wash medium. The fragments are then dried, and defatted by extraction with one or more lipophilic solvents, such as ethanol ethylacetate and diethylether, to remove lipids.

The principal mineral component of bone is calcium phosphate. The term "calcium phosphate" as used herein is intended to encompass the numerous calcium-phosphorus complexes and compounds present in bone such as the various polycalcium phosphates, hydroxyapatite, chlorapatite, and the like. Calcium phosphate usually constitutes about 80% of the mineral content of bone. Other mineral components of bone include calcium carbonate, calcium fluoride, calcium chloride, and magnesium phosphate. These minerals are normally soluble in dilute mineral and organic acids and such acids may be used to demineralize bone without digesting the protein components of the bone. The concentration of the acid used to demineralize the bone will usually be between 0.1 M to 1.0 M. Hydrochloric acid at a concentration of 0.5 M is preferred. The bone will normally be contacted with the acid for one hour to several days at temperatures ranging from about 0° C. to about 25° C. Agitation will facilitate extraction of the minerals from the bone. After the extraction is complete the bone is separated from the acid such as by sedimentation, filtration or other conventional solid-liquid separation techniques and the resulting demineralized, nondigested bone is washed with water to remove adsorbed acid.

Following demineralization noncollagenous proteins (including proteoglycans) are extracted from the demineralized bone by contacting the bone with an aqueous liquid extractant that dissociates ionic bonds and solubilizes the noncollagenous proteins in the bone. This extractant is sometimes referred to herein as a "dissociative nonfibrous protein extractant." The extraction is done under conditions that inhibit digestion or denaturation of the extracted proteins. Examples of dissociative extractants that may be used are guanidine hydrochloride (at least about 4 M), urea (8 M) plus salt (1 M), and sodium dodecyl sulfate (at least about 1% by volume). A preferred extractant is 4 M guanidine hydrochloride, pH 6.8. The extractants will usually be mixed with the bone with mild agitation at bone extractant ratios (v/w) of at least about 10:1, usually about 15:1 to 20:1. The extraction is preferably carried out at reduced temperatures in the presence of a protein inhibitor to reduce the likelihood of digestion or denaturation of the extracted protein. The temperature will usually be in the range of 0° C. and 20° C., preferably 0° C. and 5° C. Examples of protease inhibitors that may be included in the extraction medium are phenylmethylsulfonyl fluoride, N-ethyl maleimide, benzamidine, and 6-aminohexanoic acid. The pH of the extraction medium will depend upon the particular extractant that is used. The bone will usually be contacted with the extraction medium for about 16 to 24 hr. After the extraction is complete the undissolved bone is separated from the extract by conventional solid-liquid separation techniques such as centrifugation or filtration. Further work up of the extract by repeated precipitation or dialysis may be carried out if desired.

The next step in the purification of the osteogenic factor is preparative ion exchange chromatography. The chromatography is carried out in two substeps: (1) fractionation on an anion exchanger followed by (2) fractionation on a cation exchanger. In the anion exchange fractionation the noncollagenous protein extract is contacted with an anion exchanger at a pH of about 6.8 to 7.2, preferably about 7.0. Cellulosic ion exchangers and ion exchange gels derived from cross-linked dextran or polyacrylamide are examples of anion exchangers that may be used. Cellulosic anion exchangers are preferred. Diethylaminoethyl is a preferred functional anion exchange group. The anion exchange fractionation may be carried out in a column or batch operation. The noncollagenous proteins are in an aqueous solution containing one of the above-described extractants (to keep the proteins in solution) and preferably also an effective amount of a protease inhibitor when contacted with equilibrated exchanger. The solution is buffered to the desired pH. The contact time should be sufficient to allow the exchange to reach equilibrium. In a batch operation the unadsorbed fraction of the extract may be separated from the anion exchange material by centrifuging or filtering. In either instance, the unadsorbed fraction of the extract contains the desired osteogenic factor and is collected or isolated and further fractionated on the cationic exchanger.

The cation exchange fractionation is effected by contacting the unadsorbed fraction from the anion exchange substep with a cation exchanger at a pH of about 4.5 to about 5.2, preferably about 4.8. Examples of cation exchangers that may be used are the available cellulose cation exchangers and cation exchange gels derived from polyacrylamide and cross-linked dextran. Cellulosic cation exchangers are preferred. Carboxymethyl is a preferred cation exchange functional group. Before being contacted with the cation exchanger the buffers in the unadsorbed fraction of the the anion exchange step are removed from the fraction such as by dialysis. The proteins in the unadsorbed fraction are redissolved, if necessary, and the solution is buffered to the desired pH for the cation exchange. The solution is then contacted with equilibrated cation exchanger again for a time sufficient to let the exchange reach equilibrium. In the cation exchange fractionation, the fraction of the solution that is adsorbed by the cation exchanger contains the desired osteogenic factor and must be recovered from the cation exchanger. When the exchange is carried out batchwise the exchanger is first separated from the unadsorbed fraction of the solution. The exchanger is then washed with starting buffer to remove any residual unadsorbed material.

Following washing of the cation exchanger noncollagenous protein adsorbed thereon is recovered by elution with an elutant of appropriate pH or ionic strength. Stepwise or gradient elution may be used to obtain differential elution of the adsorbed proteins if desired. When carboxymethyl cellulose is used as a cation exchanger in the process the osteogenic factor may be eluted from the exchanger using a buffer having an ionic strength in the range of about 10 to about 400 mM.

The final step in the purification is fractionating the eluate by molecular weight to recover the $\leq 30K$ dalton fraction of the eluate. This fractionation may be done be gel filtration or other conventional separation techniques. Partially purified factor may be recovered from the $\leq 30K$ dalton fraction of the eluate by conventional procedures such as dialysis and lyophilization. The partially purified material may be implanted in mammals with or without a carrier to induce bone formation at the implant site.

The following example further illustrates the invention process and the partially purified osteogenic factor produced thereby. This example is not intended to limit the invention in any manner.

PREPARATION OF DEMINERALIZED BONE

Bovine metatarsal bone obtained fresh from a slaughterhouse and frozen at $-70°$ C. was used. The bone was cleaned of periosteum, broken into fragments smaller than 1 cm in diameter and pulverized in a large mill. The pulverized bone was washed overnight in 0.01 N HCl at 4° C. It was then defatted by 3 washes of approximately 20 min duration with 3 volumes of ethanol and the same with diethylether. The defatted bone powder was demineralized in 0.5 N HCl at 4° C. The acid was removed and the demineralized bone powder was washed twice with 10 volumes of water.

EXTRACTION OF NONCOLLAGENOUS PROTEINS

Demineralized bone powder was extracted with 10 volumes of 4 M guanidine-HCl, 15 mM ethylenediaminetetraacetic acid (EDTA) pH 6.5, 1 mM phenylmethylsulfonyl fluoride (PMSF), and 10 mM N-ethylmaleimide (NEM) for 16 hr at 4° C. The suspension was centrifuged at 10,000 rpm for 30 min. The pellet was washed with another five volumes of 4 M guanidine solution and centrifuged as above. Soluble fractions were combined and concentrated at least five volumes by ultrafiltration using an Amicon ultrafiltration (10K) unit. The concentrate was dialyzed employing the same unit against a solution containing 6 M urea, 1 mM PMSF, 1 mM NEM, 20 mM Na phosphate (pH 7.0) and 50 mM NaCl or dialyzed against water and lyophilized.

PREPARATIVE ION EXCHANGE

An anion exchanger, diethylaminoethyl (DEAE)-cellulose (Whatman), equilibrated with 6 M urea, 1 mM PMSF, 1 mM NEM, 20 mM Na phosphate (pH 7.0), and 50 mM NaCl was used in the first step of the ion exchange purification of the extract. The soluble extract or lyophilized extract was equilibrated or dissolved in DEAE-cellulose equilibration buffer and mixed with the exchanger and stirred gently over a period of one to two hr. The unadsorbed materials were recovered using a filtering flask followed by extensive dialysis against water and lyophilization. The unadsorbed materials were further fractionated by cation exchange chromatography using carboxymethyl (CM)-celluose, which had been equilibrated with 6 M urea, 10 mM NaCl, 1 mM PMSF, 1 mM NEM, 50 mM Na acetate, pH 4.8. The unadsorbed material was mixed with the CM-cellulose and the slurry was used to pack a 50 cc column. The column was washed with 10 mM NaCl in the above buffer. Adsorbed proteins were eluted using a 50 mM to 400 mM NaCl gradient in the same buffer. Fractions were collected and then combined based on their absorbance and electrophoretic profiles. Optical density (OD) readings at 280 nm of the fractions were made. FIG. 1 is a plot of those readings. Fractions 23-32 were combined, dialyzed against water and lyophilized.

GEL FILTRATION

Figure 2:
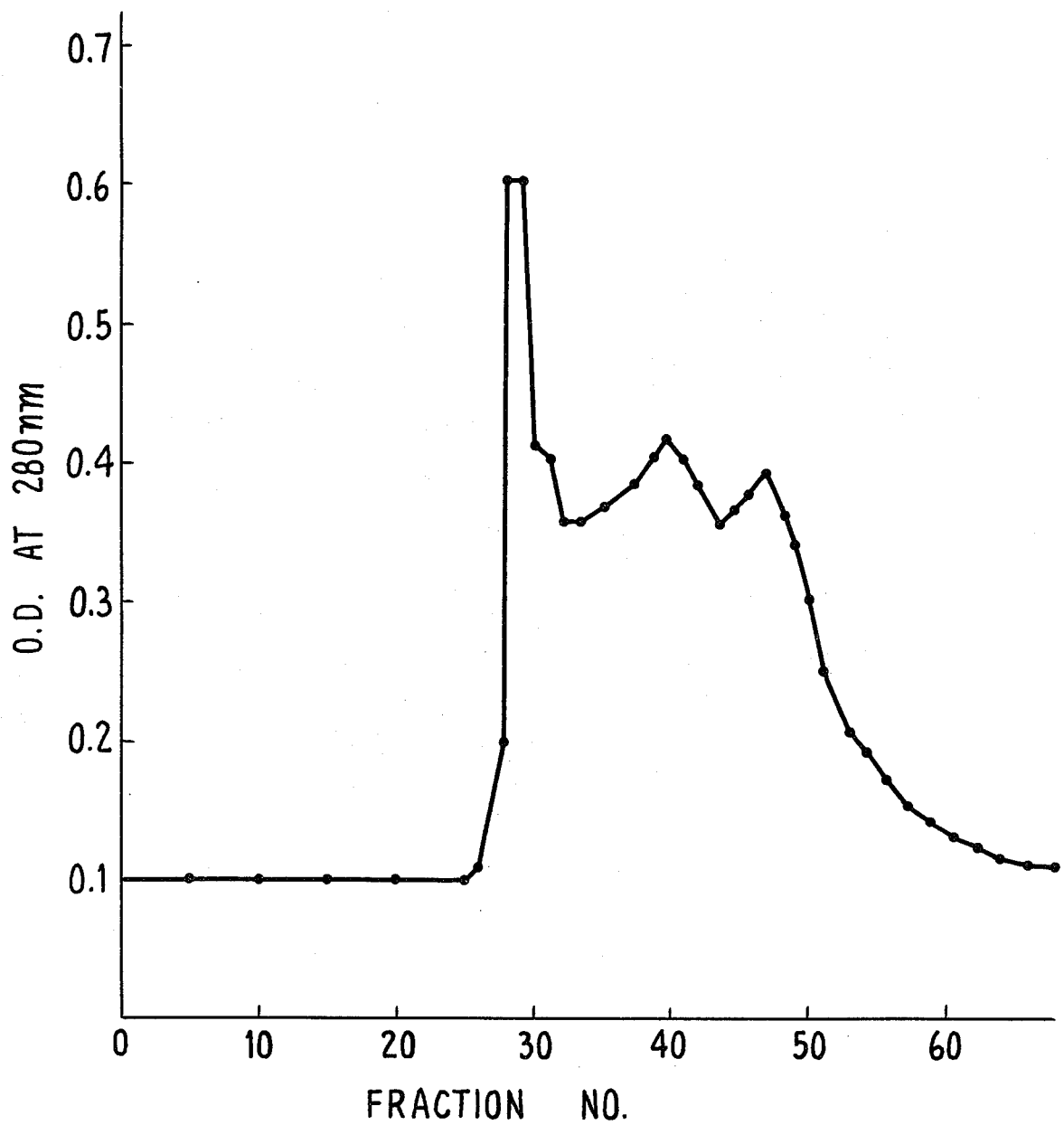
FIG. 2 is a graph of the optical densities of the gel filtration fractions of the example, infra.

The combined fraction was then fractionated on a Sephacryl S-200 column equilibrated in 6 M urea, 10 mM NaCl, 10 mM NaN$_3$, 10 mM EDTA, pH 7. OD readings at 280 nm of the fractions were made. FIG. 2 is a plot of those readings. Fractions 45-53 were combined and constitute the S-200 low molecular weight (≦30K dalton) protein fraction. This fraction was dialyzed against 0.05 N NH$_3$HCO$_3$ and lyophilized.

The osteoinductive activities of various fractions reported in the above example were assayed by their ability to cause rat muscle fibroblasts in agarose to synthesize type II collagen and cartilage proteoglycans. The materials and method used in the assay were as follows:

Muscle tissue was aseptically dissected from the upper limbs of 19 day old Sprague Dawley rat fetuses. The tissues were minced and cultured in Eagle's minimum essential medium (MEM) with 10% fetal calf serum and 50 U penicillin, 50 μg streptomycin/ml media. Cellular outgrowth usually reached confluency within one week. Cells were trypsinized at confluency, split 1:2 and used for experimentation within the first three passages.

Cells were embedded in agarose gels by the method described in *Cell* (1982) 30:215-224. Briefly, 1.0 ml of 1% high melting agarose (Bio-Rad, #162-0100) was added to each 35 mm well and allowed to gel on a level surface at room temperature. Low melting agarose, 2%, (Bio-Rad, #162-0017) equilibrated to 38° C. was mixed with an equal volume of 2X concentrated Ham's F-12 nutrient mixture and held at 38° C. The agarose/F-12 solution was then mixed with an equal volume of cell suspension and 1.5 ml was added to each well. When firm, gels were overlaid with 3.0 ml of media, cultured at 37° C. in 5% CO$_2$, 95% air and fed twice weekly. Media for cell suspension and feeding consisted of Ham's F-12 with 10% heat-inactivated fetal calf serum, 0.5% chick embryo extract (optional), penicillin/streptomycin and supplemented with the test fraction. Agarose solutions were sterilized by autoclaving at 121° C. for 15 min prior to use. The final cell concentration was 3×10$^6$ cells/35 mm well. Cultures were done in duplicate.

After 21 days of culture, gels were fixed and stained according to the method described in J Cell Biol (1970) 45:434-438. Gels were briefly rinsed two times in phosphate buffered saline (PBS), fixed in 40% formalin, rinsed with distilled water stained with 0.5% toluidine blue in 25% acetone and washed overnight with distilled water.

After fixation, a portion of each gel was removed for histological processing. Gels were dehydrated, cleared and embedded in paraffin. Four to six μm sections were taken perpendicular and parallel to the surface of the gel. Sections were stained with toluidine blue or safranin O. Proteoglycan matrix deposition was determined by metachromatic staining (purple with toludine blue, orange with safranin O).

Proteoglycans and collagen were extracted from the gels treated with extract for 3, 7, 14 days by homogenization in 2 volumes of 6 M guanidine-HCl, 0.075 M sodium acetate, 20 mM EDTA, 2 mM PMSF, 10 mM NEM, pH 5.8 followed by shaking at 4° C. for 18 hr. Agarose was removed by centrifugation (15K rpm, 30 min). The supernatant was then dialyzed against 10 volumes of water at 4° C. containing 0.2 mM PMSF (final guanidine HCl concentration ∼0.05 M). Samples were lyophilized and resuspended in 1/10 volume water (final guanidine HCl concentration ∼0.5 M).

Proteoglycans and type II collagen were then measured by the enzyme-linked immunosorbent assaay (ELISA) technique essentially as described by Rennard, et al., *Anal Biochem* (1980) 104:205-214. Antisera to cartilage proteoglycans and type II collagen were raised in rabbits using standard techniques. Both proteoglycan and type II collagen for immunization were isolated from Swarm rat chondrosarcomas. Antisera to type II collagen was affinity purified using a cyanogen bromide Sepharose column.

For ELISA, microtiter wells were coated with 200 μl of the appropriate antigen in 20 mM carbonate buffer, pH 9.6, at 4° C. overnight (100-10000 ng/well). Wells were washed 3 times with 0.9% NaCl containing 0.05% Tween 20 surfactant to remove unbound antigen. Proteoglycans and type II collagen were measured by inhibition ELISA. Sample aliquots (10-100 μl) were incubated in PBS containing 1 mg/ml bovine serum albumin and 0.05% Tween 20 surfactant with the appropriate antisera (1:500 affinity purified type II or 1:2000 proteoglycan) for 2 hr at room temperature. Two hundred μl of incubation mixture was then added to antigen-coated plates for 45-60 min at room temperature. After washing 3 times with PBS-Tween 20 surfactant, goat anti-rabbit IgG conjugated to horseradish peroxidase (Tago, 1:200) was then added for one hr at room temperature. Unbound second antibody was then removed with PBS-Tween 20 surfactant and substrate (o-phenylenediamine, 1 mg/ml in 0.1 M citrate, pH 4.6) was added for 30-60 min. Reactions were stopped by addition of 50 μl 2 M sulfuric acid. Spectrophotometric readings (492 nm) of the reaction media were done and compared to standard curves to determine whether production of type II collagen and proteoglycan had been induced. The results of these assays (+ indicates induction, − indicates no induction) are tabulated below.

| Fraction | Type II collagen | Proteoglycans |
|---|---|---|
| Control | − | − |
| Extract | + | + |
| DEAE adsorbed | − | − |
| DEAE unadsorbed | + | + |
| CM adsorbed | + | + |
| CM unadsorbed | − | − |
| Sephacryl S-200 ( 30K dalton fraction) | + | + |
| Sephacryl S-200 | − | − |

| Fraction | Type II collagen | Proteoglycans |
|---|---|---|
| ( 30K dalton fraction) | | |

Modifications of the above described modes for carrying out the invention that are obvious to those of skill in the biochemistry, chromatography, ostoplasty, and related fields are intended to be within the scope of the following claims.

We claim:

1. A process for partially purifying an osteogenic factor from particulate demineralized bone comprising:
   (a) extracting nonfibrous proteins from the demineralized bone with a liquid dissociative nonfibrous protein extractant;
   (b) contacting the extract of (a) with an anion exchanger at a pH of about 6.8 to about 7.2.
   (c) contacting the unadsorbed fraction of the extract with a cation exchanger at a pH of about 4.5 to about 5.2;
   (d) eluting the adsorbed fraction from the cation exchanger; and
   (e) isolating nonfibrous protein having a molecular weight below about 30,000 daltons from the eluate of (d).

2. The process of claim 1 wherein steps (a) through (d) are each carried out in the presence of a protease inhibitor.

3. The process of claim 1 wherein the extractant is urea or guanidine hydrochloride.

4. The process of claim 1 wherein the extractant is 4 M guanidine hydrochloride.

5. The process of claim 1 wherein the anion exchanger and the cation exchanger are cellulosic ion exchangers.

6. The process of claim 5 wherein the anion exchanger is diethylaminoethyl cellulose and the cation exchanger is carboxymethyl cellulose; step (b) is carried out at a pH of about 7.0; and step (c) is carried out at a pH of about 4.8.

7. The process of claim 1 wherein step (e) is carried out by gel filtration.

8. The process of claim 2 wherein the extractant is 4 M guanidine, the extractant is removed from the extract, the nonfibrous proteins in the extract are dissolved in 6 M urea for contacting with the anion exchanger, the anion exchanger is diethylaminoethyl cellulose, the pH of step (b) is about 7.0, the cation exchanger is carboxymethyl cellulose, and the pH of step (c) is about 4.8.

9. Partially purified osteogenic factor prepared by the process of claim 1.

10. Partially purified osteogenic factor prepared by the process of claim 8.

* * * * *